United States Patent
Xu et al.

(10) Patent No.: US 7,845,931 B2
(45) Date of Patent: Dec. 7, 2010

(54) POLYMERIZATION TECHNIQUE TO ATTENUATE OXYGEN INHIBITION OF SOLIDIFICATION OF LIQUIDS AND COMPOSITION THEREFOR

(75) Inventors: Frank Y. Xu, Round Rock, TX (US); Edward Brian Fletcher, Austin, TX (US); Pankaj B. Lad, DeSoto, TX (US); Michael P. C. Watts, Austin, TX (US)

(73) Assignee: Molecular Imprints, Inc., Austin, TX (US)

( * ) Notice: Subject to any disclaimer, the term of this patent is extended or adjusted under 35 U.S.C. 154(b) by 77 days.

(21) Appl. No.: 11/858,687

(22) Filed: Sep. 20, 2007

(65) Prior Publication Data

US 2008/0085465 A1    Apr. 10, 2008

Related U.S. Application Data

(63) Continuation of application No. 10/948,511, filed on Sep. 23, 2004, now abandoned.

(51) Int. Cl.
  *B29C 59/00*  (2006.01)
(52) U.S. Cl. ....................... 425/385; 264/293
(58) Field of Classification Search ................. 425/385; 264/293
See application file for complete search history.

(56) References Cited

U.S. PATENT DOCUMENTS

| | | | |
|---|---|---|---|
| 3,844,916 A | 10/1974 | Gaske | |
| 4,058,656 A | 11/1977 | Markiewitz et al. | |
| 4,118,235 A * | 10/1978 | Horiuchi et al. | 106/38.22 |
| 4,628,112 A | 12/1986 | Winkel et al. | |
| 4,707,432 A | 11/1987 | Gatechair et al. | |
| 5,376,169 A | 12/1994 | Hotomi et al. | |
| 6,063,888 A * | 5/2000 | Yamaguchi et al. | 528/32 |
| 6,306,557 B1 | 10/2001 | Lin et al. | |
| 6,696,220 B2 | 2/2004 | Bailey et al. | |
| 6,719,915 B2 | 4/2004 | Willson et al. | |
| 6,900,881 B2 | 5/2005 | Sreenivasan et al. | |
| 6,936,194 B2 | 8/2005 | Watts | |
| 7,090,716 B2 | 8/2006 | McMackin et al. | |

(Continued)

FOREIGN PATENT DOCUMENTS

CN    1519260 A    8/2004

(Continued)

OTHER PUBLICATIONS

Arsu et al. Factors affecting the photoyellowing which occurs during the photoinitiated polymerization of acrylates; Journal of Photochemistry and Photobiology A: 87 (1995) 169-175; Sep. 14, 1994.

(Continued)

*Primary Examiner*—Maria Veronica D Ewald
(74) *Attorney, Agent, or Firm*—Heather L. Flanagan

(57) ABSTRACT

The present invention includes a method of solidifying a polymerizable liquid to form a film on a substrate that features minimizing inhibition of the polymerization process by oxygen contained in the atmosphere surrounding the polymerizable liquid. To that end, the polymerizable liquid includes, inter alia, an initiator that consumes oxygen that interacts with the polymerizable liquid and generates additional free radicals to facilitate the polymerizable process.

20 Claims, 4 Drawing Sheets

U.S. PATENT DOCUMENTS

| | | |
|---|---|---|
| 7,309,225 B2 | 12/2007 | McMackin et al. |
| 7,365,103 B2 | 4/2008 | Willson et al. |
| 2003/0235787 A1 | 12/2003 | Watts et al. |
| 2004/0046288 A1 | 3/2004 | Chou |
| 2004/0065252 A1 | 4/2004 | Sreenivasan et al. |
| 2004/0065976 A1 | 4/2004 | Sreenivasan et al. |
| 2004/0137734 A1 | 7/2004 | Chou et al. |
| 2004/0219306 A1* | 11/2004 | Wang et al. ............... 428/1.5 |
| 2005/0098534 A1 | 5/2005 | Sreenivasan et al. |
| 2005/0187339 A1 | 8/2005 | Xu et al. |
| 2006/0062922 A1 | 3/2006 | Xu et al. |
| 2007/0021520 A1 | 1/2007 | Xu |
| 2007/0141271 A1 | 6/2007 | Xu et al. |

FOREIGN PATENT DOCUMENTS

| | | |
|---|---|---|
| GB | 1216105 A | 12/1970 |
| TW | 101410 | 7/1988 |
| WO | 2004/013693 A2 | 2/2004 |
| WO | WO2004013693 A2 | 2/2004 |
| WO | WO2006036562 A2 | 4/2006 |

OTHER PUBLICATIONS

Kim et al. Vinyl ethers in ultraviolet curable formulations for step and flash imprint lithography; J. Vac. Sci. Technol. B, vol. 22, No. 1; Jan. 15, 2004.

Studer et al. Overcoming oxygen inhibition in UV-curing of acrylate coatings by carbon dioxide inerting: Part II; Progress in Organic Coatings 48 (2003) 101-111; Jul. 1, 2003.

International Search Report for Application No. PCT/US05/32804; dated Jan. 31, 2007, 8 pages Decker, C., et al.; Real-time kinetic study of laser-induced polymerization; American Chemical Society. Macromolecules, vol. 22, No. 12, 1989, pp. 4455-4462.

Bender et al., Multiple Imprinting in UV-based Nanoimprint Lithography: Related Material Issues, Microelectronic Engineering 61-62 (2002) pp. 407-413.

* cited by examiner

POLYMERIZATION TECHNIQUE TO ATTENUATE OXYGEN INHIBITION OF SOLIDIFICATION OF LIQUIDS AND COMPOSITION THEREFOR

CROSS-REFERENCE TO RELATED APPLICATION

This application is a continuation of United States patent publication no. 2006-0062922-A1, filed Sep. 23, 2004 as Ser. No. 10/948,511, entitled POLYMERIZATION TECHNIQUE TO ATTENUATE OXYGEN INHIBITION OF SOLIDIFICATION OF LIQUIDS AND COMPOSITION THEREFOR, naming Frank Y. Xu, Edward B. Fletcher, Pankaj B. Lad, and Michael P. C. Watts as inventors, and which is incorporated herein by reference.

STATEMENT REGARDING FEDERALLY SPONSORED RESEARCH OR DEVELOPMENT

The United States government has a paid-up license in this invention and the right in limited circumstance to require the patent owner to license others on reasonable terms as provided by the terms of 70NANB4H3012 awarded by National Institute of Standards (NIST) ATP Award.

BACKGROUND OF THE INVENTION

The field of invention relates generally to micro-fabrication of structures. More particularly, the present invention is directed to a polymerization technique suited for use in imprint lithography.

Micro-fabrication involves the fabrication of very small structures, e.g., having features on the order of micro-meters or smaller. One area in which micro-fabrication has had a sizeable impact is in the processing of integrated circuits. As the semiconductor processing industry continues to strive for larger production yields while increasing the circuits per unit area formed on a substrate, micro-fabrication becomes increasingly important. Micro-fabrication provides greater process control while allowing increased reduction of the minimum feature dimension of the structures formed. Other areas of development in which micro-fabrication has been employed include biotechnology, optical technology, mechanical systems and the like.

An exemplary micro-fabrication technique is commonly referred to as imprint lithography and is described in detail in numerous publications, such as United States published patent applications no. 2004/0065976 entitled METHOD AND A MOLD TO ARRANGE FEATURES ON A SUBSTRATE TO REPLICATE FEATURES HAVING MINIMAL DIMENSIONAL VARIABILITY; no. 2004/0065252, entitled METHOD OF FORMING A LAYER ON A SUBSTRATE TO FACILITATE FABRICATION OF METROLOGY STANDARDS; and No. 2004/0046271, entitled METHOD AND A MOLD TO ARRANGE FEATURES ON A SUBSTRATE TO REPLICATE FEATURES HAVING MINIMAL DIMENSIONAL VARIABILITY, all of which are assigned to the assignee of the present invention. The fundamental imprint lithography technique as shown in each of the aforementioned published patent applications includes formation of a relief pattern in a polymerizable layer and transferring the relief image into an underlying substrate forming a relief image in a structure. To that end, a template is employed spaced-apart from a substrate, with a formable liquid present between the template and the substrate. The liquid is solidified forming a solidified layer that has a pattern recorded therein that is conforming to a shape of the surface of the template in contact with the liquid. The substrate and the solidified layer are then subjected to processes to transfer, into the substrate, a relief structure that corresponds to the pattern in the solidified layer.

One manner in which the polymerizable liquid is located between the template and the substrate is by depositing a plurality of droplets of liquid on the substrate. Thereafter, contact is made with the polymerizable liquid by the template to spread the polymerizable liquid over the surface of the substrate and subsequently record a pattern therein. It is highly desirable to avoid trapping of gases, such as air, when the polymerizable liquid spreads over the substrate.

It is desired, therefore, to provide a method for forming a fluid layer on a substrate while minimizing the trapping of gases therein.

SUMMARY OF THE INVENTION

The present invention includes a method of solidifying a polymerizable liquid to form a film on a substrate that features minimizing inhibition of the polymerization process by oxygen contained in the atmosphere surrounding the polymerizable liquid. To that end, the polymerizable liquid includes, inter alia, an initiator or additive that consumes oxygen that interacts with the polymerizable liquid and generates additional free radicals to facilitate the polymerization process. Specifically, the method includes creating a primary group of free radicals by exposing the polymerizable liquid to actinic radiation to initiate linking together of a plurality of molecules. A secondary group of free radicals is generated by interaction of molecules of an atmosphere surrounding the liquid by a subset of the free radicals of the primary group. A tertiary group of free radicals is generated by interaction of the plurality of molecules with the free radicals of the secondary group to link together additional molecules of the plurality of molecules. These and other embodiments are discussed more fully below.

DETAILED DESCRIPTION OF THE INVENTION

Figure 1:
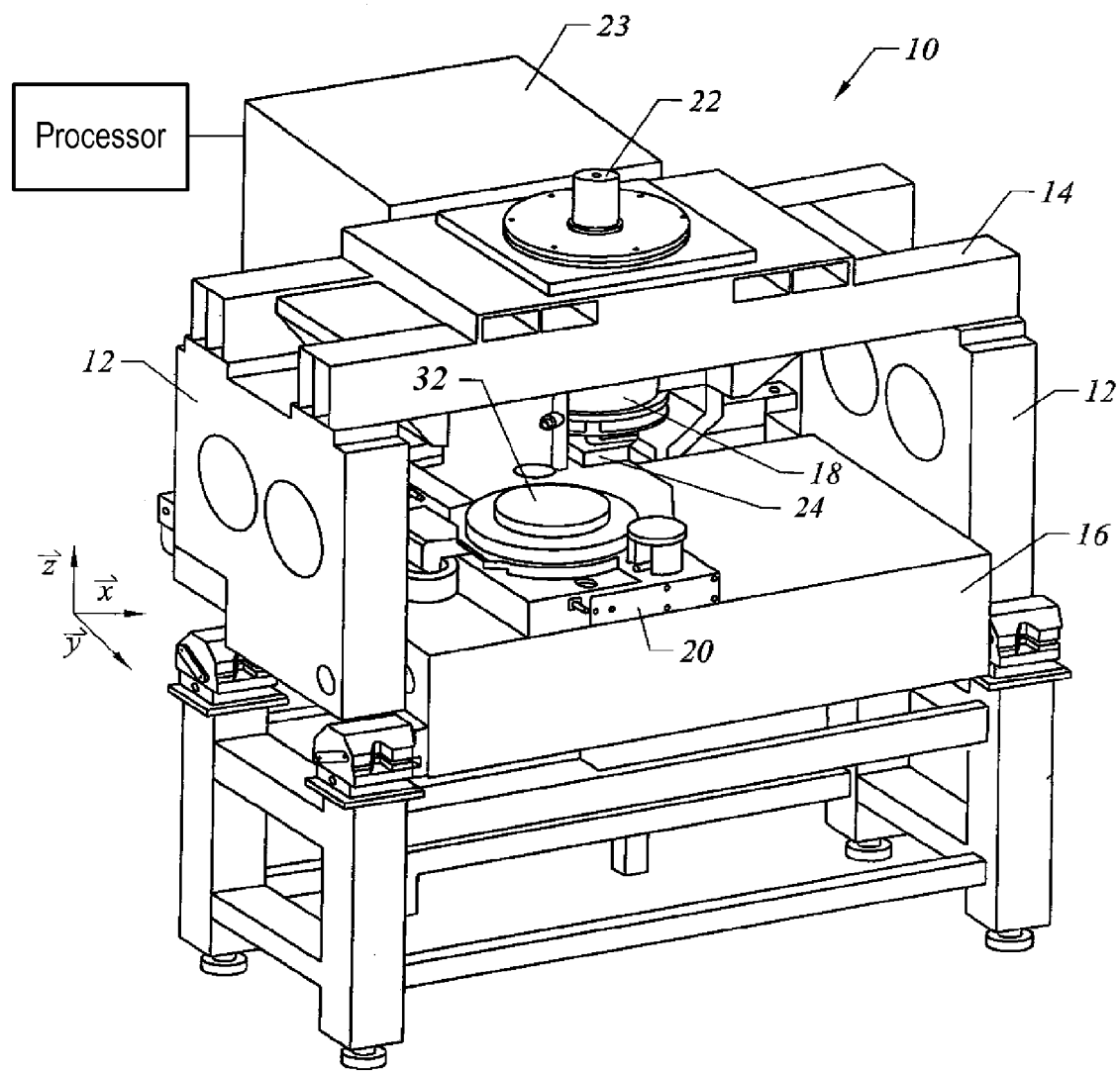
FIG. 1 is a perspective view of a lithographic system in accordance with the present invention.

FIG. 1 depicts a lithographic system 10 in accordance with one embodiment of the present invention that includes a pair of spaced-apart bridge supports 12 having a bridge 14 and a stage support 16 extending therebetween. Bridge 14 and stage support 16 are spaced-apart. Coupled to bridge 14 is an imprint head 18, which extends from bridge 14 toward stage support 16. Disposed upon stage support 16 to face imprint head 18 is a motion stage 20. Motion stage 20 is configured to move with respect to stage support 16 along X and Y axes and may provide movement along the Z axis as well. A radiation source 22 is coupled to system 10 to impinge actinic radiation upon motion stage 20. As shown, radiation source 22 is coupled to bridge 14 and includes a power generator 23 connected to radiation source 22.

Figure 2:
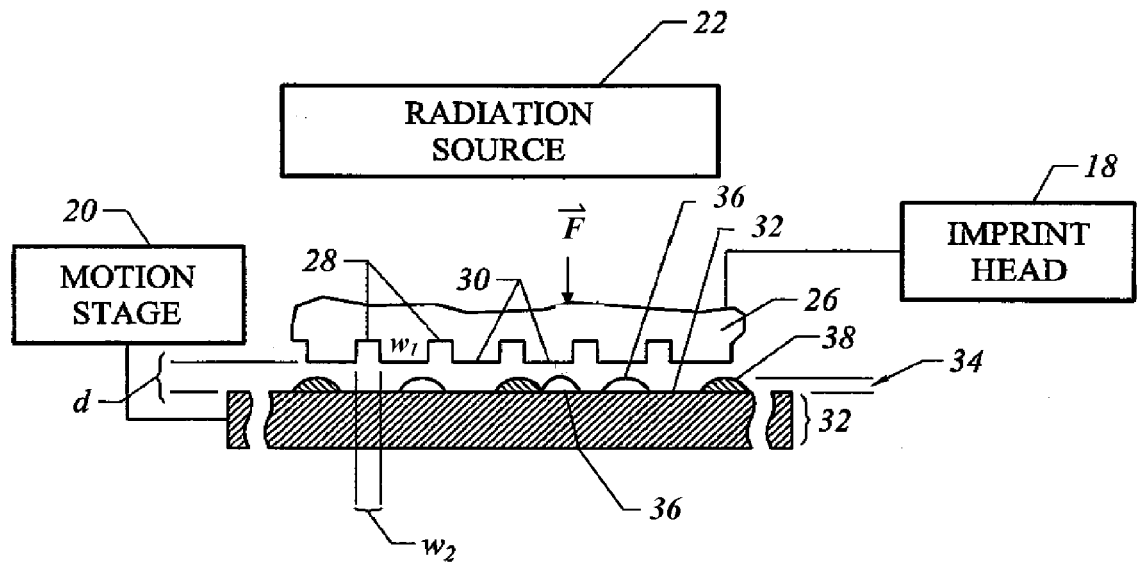
FIG. 2 is a simplified elevation view of a lithographic system, shown in FIG. 1, employed to create a patterned imprinting layer in accordance with one embodiment of the present invention.

Referring to both FIGS. 1 and 2, connected to imprint head 18 is template 24 having mold 26 thereon, which may define a smooth or planar surface having a pattern formed therein. As shown, mold 26 includes a pattern having a plurality of features defined by a plurality of spaced-apart recesses 28 and projections 30. Projections 30 have a width $W_1$, and recesses 28 have a width $W_2$, both of which are measured in a direction that extends transversely to the Z axis. The plurality of features defines an original pattern that forms the basis of a pattern to be transferred into a substrate 32 positioned on motion stage 20. To that end, imprint head 18 is adapted to move along the Z axis and vary a distance "d" between mold 26 and substrate 32. Alternatively, or in conjunction with imprint head 18, motion stage 20 may move template 24 along the Z-axis. In this manner, the features on mold 26 may be imprinted into a flowable region of substrate 32, discussed more fully below.

Radiation source 22 is located so that mold 26 is positioned between radiation source 22 and substrate 32, with actinic radiation generated by radiation source 22 propagating through mold 26. As a result, it is desired that mold 26 be fabricated from material that is substantially transparent to the actinic radiation. Exemplary materials from which mold 26 may be fabricated include fused-silica, quartz, silicon, organic polymers, siloxane polymers, borosilicate glass, fluorocarbon polymers, metal, and combinations of the above dependent upon the actinic radiation employed. An exemplary system is available under the trade name IMPRIO® 100 from Molecular Imprints, Inc. having a place of business at 1807 Braker Lane, Building C-100, Austin, Tex. 78758. The system description for the IMPRIO® 100 is available at www.molecularimprints.com and is incorporated herein by reference.

Figure 3:
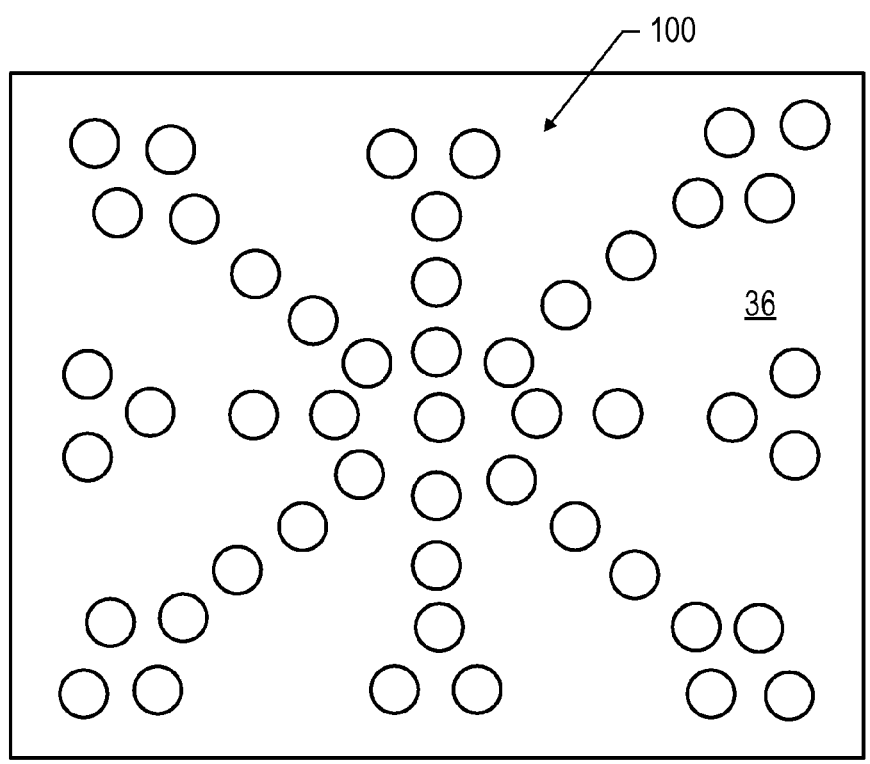
FIG. 3 is a top-down view of a region of the substrate, shown in FIG. 2, upon which patterning occurs employing a pattern of droplets of polymerizable fluid disposed thereon.

Referring to both FIGS. 2 and 3, a flowable region, such as an imprinting layer 34, is formed on a portion of surface 36 that presents a substantially smooth, if not planar, profile of a surface facing mold 26. In one embodiment of the present invention, the flowable region is deposited as a plurality of spaced-apart discrete droplets 38 of imprinting material on substrate 32. Specifically, droplets 38 are arranged on surface 36 in a pattern 100 that minimizes trapping of gases when the imprinting material of droplets 38 merges to form a contiguous layer over surface 36, shown more clearly in FIG. 4 as recorded pattern 134.

Figure 4:
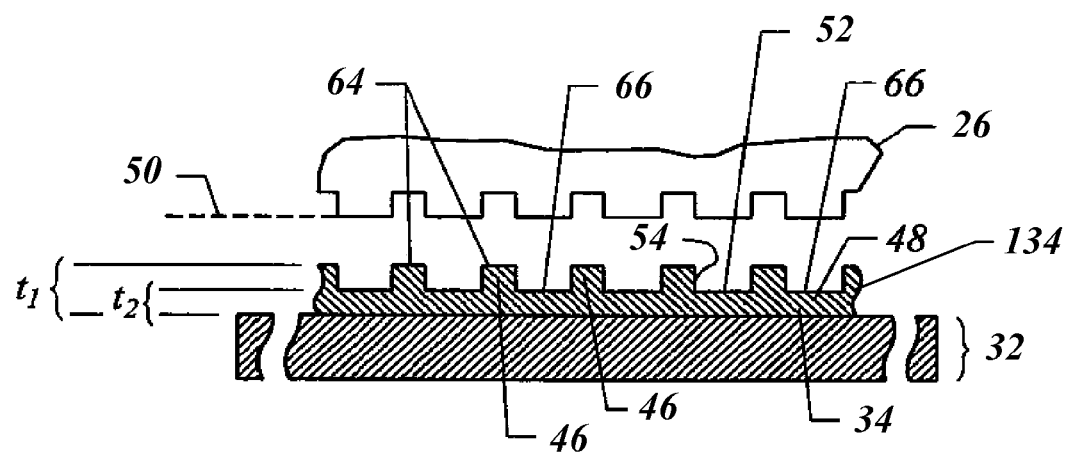
FIG. 4 is a simplified elevation view of an imprint device spaced-apart from the patterned imprinting layer, shown in FIG. 1, after patterning in accordance with the present invention.

Referring to both FIGS. 2 and 4, the imprinting material may be selectively polymerized and cross-linked to record an inverse of the original pattern therein, defining a recorded pattern 134 that is subsequently solidified as discussed below. The plurality of features on mold 26 are shown as recesses 28 extending along a direction parallel to projections 30 that provide a cross-section of mold 26 with a shape of a battlement. However, recesses 28 and projections 30 may correspond to virtually any feature desired and may be as small as a few tenths of nanometers: features such as those that facilitate formation of integrated circuits.

Figure 5:
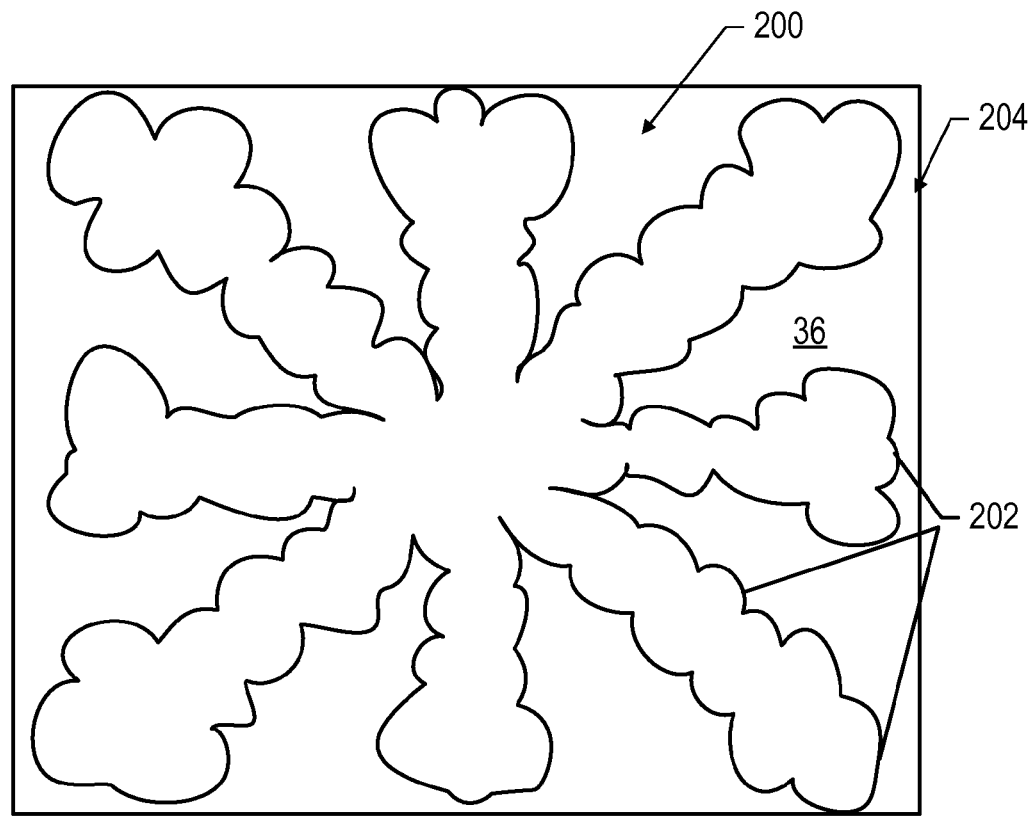
FIG. 5 is a top-down view of a region of the substrate, shown in FIG. 4, showing an intermediate pattern formed by the droplets of polymerizable fluid shown in FIG. 4, during spreading.

Referring to both FIGS. 2 and 5, the recorded pattern 134 is produced, in part, by interaction of the imprinting material with mold 26, e.g., mechanical contact, electrical contact and the like. In an exemplary embodiment, distance "d" is reduced to allow imprinting layer 34 to come into mechanical contact with mold 26. In response, the imprinting material in droplets 38 spreads forming a series of intermediate patterns, one of which is shown as pattern 200, to form a contiguous formation of the imprinting material over surface 36. In one embodiment, distance "d" is reduced to allow sub-portions 46 of recorded pattern 134 to ingress into and fill recesses 28. It may be desired to purge the volume, for example with Helium gas flowed at 5 pounds per square inch (psi), defined between mold 26 and both surface 36 and droplets 38 before contact occurs. An exemplary purging technique is disclosed in U.S. Pat. No. 7,090,716, filed Oct. 2, 2003 as Ser. No. 10/677,639, entitled SINGLE PHASE FLUID IMPRINT LITHOGRAPHY METHOD, and which is incorporated by reference herein.

In the present embodiment, sub-portions 48 of recorded pattern 134 in superimposition with projections 30 remain after the desired, usually minimum distance "d", has been reached, leaving sub-portions 46 with a thickness $t_1$, and sub-portions 48 with a thickness, $t_2$. Thickness $t_2$ is referred to as a residual thickness. Thicknesses "$t_1$" and "$t_2$" may be any thickness desired, dependent upon the application. The total volume contained in droplets 38 may be such so as to minimize, or avoid, a quantity of the imprinting material from extending beyond the region of surface 36 in superimposition with mold 26, while obtaining desired thicknesses $t_1$ and $t_2$, i.e., through capillary attraction of the imprinting material with mold 26 and surface 36 and surface adhesion of the imprinting material.

Referring again to FIGS. 2 and 3, after a desired distance "d" has been reached, radiation source 22 produces actinic radiation that polymerizes and cross-links the imprinting material, solidifying recorded pattern 134. The composition of imprinting layer 34 transforms from a fluidic imprinting material to a solidified material. This provides solidified imprinting layer 134 with a side having a shape that conforms to a shape of a surface 50 of mold 26, shown more clearly in FIG. 4. As a result, recorded pattern 134 is formed having recessions 52 and protrusions 54. After solidification of recorded pattern 134, distance "d" is increased so that mold 26 and recorded pattern 134 are spaced-apart. Typically, this process is repeated several times to pattern different regions (not shown) of substrate 32, referred to as a step and repeat process. An exemplary step and repeat process is disclosed in U.S. Pat. No. 6,900,881, filed Jul. 11, 2002 as Ser. No. 10/194,414, entitled STEP AND REPEAT IMPRINT LITHOGRAPHY, which is assigned to assignee of the present invention and is incorporated by reference.

The advantages of this patterning process are manifold. For example, the thickness differential between protrusions 54 and recessions 52 facilitates formation, in substrate 32, of a pattern corresponding to the recorded pattern 134. Specifically, the thickness differential between $t_1$ and $t_2$ of protrusions 54 and recession 52, respectively, results in a greater amount of etch time being required before exposing regions of substrate 32 in superimposition with protrusions 54 compared with the time required for regions of substrate 32 in superimposition with recession 52 being exposed. For a given etching process, therefore, etching will commence sooner in regions of substrate 32 in superimposition with recessions 52 than regions in superimposition with protrusions 54. This facilitates formation of a pattern in substrate corresponding to recorded pattern 134. By properly selecting the imprinting materials and etch chemistries, the relational dimensions between the differing features of the pattern eventually transferred into substrate 32 may be controlled as desired. To that end, it is desired that the etch characteristics of recorded pattern 134, for a given etch chemistry, be substantially uniform.

As a result, the characteristics of the imprinting material are important to efficiently pattern substrate 32 in light of the unique patterning process employed. As mentioned above, the imprinting material is deposited on substrate 32 as a plurality of discrete and spaced-apart droplets 38. The combined volume of droplets 38 is such that the imprinting material is distributed appropriately over an area of surface 36 where recorded pattern 134 is to be formed. In this fashion, the total volume of the imprinting material in droplets 38 defines the distance "d", to be obtained so that the total volume occupied by the imprinting material in the gap defined between mold 26 and the portion of substrate 32 in superimposition therewith once the desired distance "d" is reached is substantially equal to the total volume of the imprinting material in droplets 38. To facilitate the deposition process, it is desired that the imprinting material provide rapid and even spreading of the imprinting material in droplets 38 over surface 36 so that all thicknesses $t_1$ are substantially uniform and all residual thicknesses $t_2$ are substantially uniform.

Figure 6:
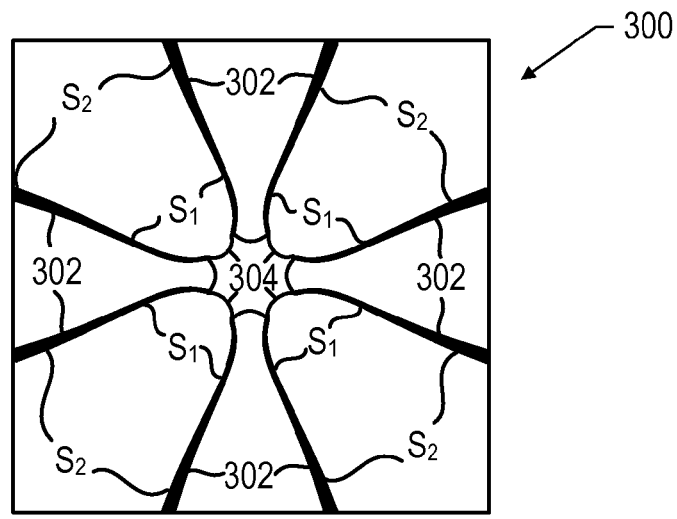
FIG. 6 is a top-down view of a layer, formed from a polymerizable material, after being subjected to ultra-violet radiation.

Referring to FIG. 6, a problem recognized by the present invention involves varying evaporation characteristics of a contiguous layer 300. Layer 300 was formed in the manner discussed above, excepting that a planarization mold (not shown), i.e., a non-patterned mold with a smooth surface, was employed to spread droplets 38. After spreading of droplets 38, the imprinting material was exposed for approximately 700 ms to actinic radiation having a wavelength of approximately 365 nm a flux of 77 mW/cm$^2$ to solidify the same. After solidification of layer 300, observed were varying thicknesses over the area thereof. Specifically, regions 302 and 304 were found to be thinner than the remaining regions of layer 300. As can be seen, regions 304 have a substantially uniform area compared to regions 302. Regions 302 have a first thickness $s_1$, proximate to regions 304, which become increasingly larger reaching an apex proximate to an outer edge of layer 300 shown as $s_2$. It is believed that regions 302 and 304 result from partial polymerization attributable to the presence of oxygen during the series of intermediate patterns that are generated as the imprinting material in droplets 38 spreads. As shown, a material-ambient boundary 202 is generated in intermediate pattern 200 as the imprinting material spreads. The material-ambient boundary 202 persists until adjacent volumes of imprinting material merges. As can be seen, the imprinting material merges earlier in central regions of pattern 200 as compared to regions of pattern 200 disposed proximate to boundary 204. It is believed that the reduction in polymerization is directly related to the length of time of exposure to the components of the ambient, such as oxygen, which is believed to cause evaporation and inhibits polymerization. This provides a rationale for the varying thickness of regions 302. The prior art composition for the imprinting material used to form layer 300 is as follows:

PRIOR ART COMPOSITION isobornyl acrylate n-hexyl acrylate ethylene glycol diacrylate 2-hydroxy-2-methyl-1-phenyl-propan-1-one $R_1R_2$ with $R_1R_2$ being a surfactant. For purposes of this invention, a surfactant is defined as any molecule, one tail of which is hydrophobic. Surfactants may be either fluorine-containing, e.g., include a fluorine chain, or may not include any fluorine in the surfactant molecule structure. In surfactant $R_1R_2$, $R_1$=F $(CF_2CF_2)_y$, with y being in a range of 1 to 7, inclusive, and $R_2$=$CH_2CH_2O(CH_2CH_2O)_xH$, with X is in a range of 0 to 15, inclusive. An exemplary surfactant is available under the trade name ZONYL® FSO-100 from DUPONT™. It was believed that during the polymerization reaction, the PRIOR ART COMPOSITION formed peroxide radicals proximate to the material-gas boundaries. This slows the rate of, if not prevents, polymerization of the imprinting material. As a result, for a given polymerization process, film 300 is provided with varying degrees of solidification over the volume thereof.

The present invention overcomes these drawbacks by including in the composition, which forms the imprinting material, a scavenger material that consumes molecules in the ambient that would inhibit the curing process. Specifically, it was found that by including an additive with the initiator, the inhibition of polymerization at material-gas boundaries could be minimized. To that end, included in the PRIOR ART COMPOSITION is an amine-containing additive to provide the following composition:

COMPOSITION 1 isobornyl acrylate n-hexyl acrylate ethylene glycol diacrylate 2-hydroxy-2-methyl-1-phenyl-propan-1-one N-methyldiethanolamine $R_1R_2$ The acrylate component isobornyl acrylate (IBOA) has the following structure:

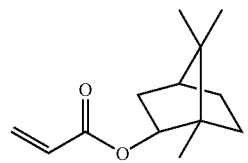

and comprises approximately 55% of COMPOSITION 1 by weight, but may be present in a range of 20% to 80%, inclusive. As a result, the mechanical properties of solidified imprinting layer 134 are primarily attributable to IBOA. The component n-hexyl acrylate (nHA) has the following structure:

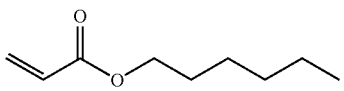

and comprises approximately 27% of COMPOSITION 1 by weight, but may be present in a range of 0% to 50%, inclusive. Also providing flexibility to solidified imprinting layer 134, nHA is employed to reduce the viscosity of the prior art composition so that COMPOSITION 1, in the liquid phase, has a viscosity in a range 2-9 Centipoises, inclusive. A cross-linking component, ethylene glycol diacrylate, has the following structure:

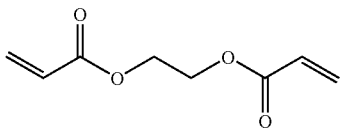

and comprises approximately 15% of COMPOSITION 1 by weight, and may be present in a range of 10% to 50%, inclusive. EGDA also contributes to the modulus and stiffness buildup, as well as facilitates cross-linking of nHA and IBOA during polymerization of COMPOSITION 1. An initiator component, 2-hydroxy-2-methyl-1-phenyl-propan-1-one is available from Ciba Specialty Chemicals of Tarrytown, N.Y. under the trade name DAROCUR 1173, has the following structure:

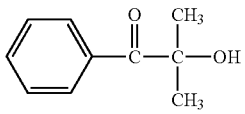

and comprises approximately 3% of COMPOSITION 1 by weight, and may be present in a range of 1% to 5%, inclusive. The initiator is responsive to a broad band of ultra-violet radiation generated by a medium-pressure mercury lamp. In this manner, the initiator facilitates cross-linking and polymerization of the components of COMPOSITION 1. A surfactant component, $R_1R_2$, is as described above with respect to the PRIOR ART COMPOSITION and has the following general structure:

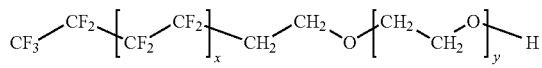

The surfactant component provides suitable wetting properties of COMPOSITION 1 when in the liquid phase, as well as desired release characteristics in the solid phase. An amine component N-methyldiethanolamine has the following structure:

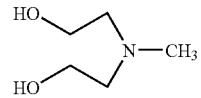

and comprises approximately 0.5% to 4%, inclusive of COMPOSITION 1 by weight. The amine component reduces, if not prevents, the deleterious effects of the ambient on COMPOSITION 1. Specifically, the following reactions occur during polymerization:

$$\text{initiator} \xrightarrow{h\nu} R\cdot \quad (1)$$

where the initiator is 2-hydroxy-2-methyl-1-phenyl-propan-1-one, hν is the optical energy generated by the ultraviolet radiation impinging upon the initiator and R• is a primary group of free radicals generated by the initiator in response to the radiation. The free primary group of free radicals then interact with the IBOA and nHA acrylates, M, as follows:

$$R\cdot + M \to RM\cdot \xrightarrow{M} P\cdot(RMM\cdot) \quad (2)$$

where RM• is a radical chain also denoted as P• and terminates into polymer chains as follows:

$$P\bullet + P\bullet \to \text{Polymer} \quad (3)$$

In addition to reactions 1-3 above, additional reactions occur proximate to boundary 202 where the ambient is present. An exemplary reaction occurs between the radical initiator R• and oxygen $O_2$ as follows:

$$R\bullet + O_2 \to RO_2\bullet \quad (4)$$

where $RO_2\bullet$ is a secondary group of radicals, i.e., peroxide radicals. The peroxide radical is undesirable in that it effectively consumes the radicals of the primary group R• reducing the quantity of the same to facilitate the reaction of equation (2) and the peroxide radical itself has a low probability of initiating polymerization. This inhibits polymerization as defined by equation (4). The amine group, DH, of COMPOSITION 1, however, reacts with the secondary group of radicals $RO_2\bullet$ to produce a tertiary group of radicals D•, as well as some residual molecules $RO_2H$ as follows:

$$RO_2\bullet + DH \to RO_2H + D\bullet \quad (5)$$

In addition, the amine radical reacts with the acrylates M to facilitate further polymerization thereof as follows:

$$D\bullet + M \to DM\bullet \quad (6)$$

Also, the amine group reacts with oxygen present in the ambient to reduce the formation of the $RO_2\bullet$ type of peroxide radicals, as follows:

$$D\bullet + O_2 \to DO_2\bullet \quad (7)$$

Although the radical $DO_2\bullet$ is undesirable, the same may interact with other amine groups present in COMPOSITION 1 as follows:

$$DO_2\bullet + DH \to DO_2H + D\bullet \quad (8)$$

that creates additional radicals D• to further polymerization while reducing the presence of oxygen in solidified imprinting layer by as much as 99%. It should be understood that the amine group may be included in COMPOSITION 1 by replacing, or using in conjunction with the 2-hydroxy-2-methyl-1-phenyl-propan-1-one initiator, an amine-containing initiator that may be included with the tertiary amine component or in lieu thereof. Were the amine group employed in lieu of the initiator, it is desirable that the amine group be photoactive in generating radical upon UV exposure. To that end, other compositions may include the following:

COMPOSITION 2 isobornyl acrylate n-hexyl acrylate ethylene glycol diacrylate

2-Methyl-1[4-(methylthio)phenyl]-2-morpholinopropan-1-one $R_1R_2$ where 2-Methyl-1[4-(methylthio)phenyl]-2-morpholinopropan-1-one is available from Ciba Specialty Chemicals Corporation of Tarrytown N.Y. under the trade name IRGACURE® 907; and

COMPOSITION 3 isobornyl acrylate n-hexyl acrylate ethylene glycol diacrylate

2-Benzyl-2-dimethylamino-1-(4-morpholinophenyl)-1-butanone $R_1R_2$ where 2-Benzyl-2-dimethylamino-1-(4-morpholinophenyl)-1-butanone is available from Ciba Specialty Chemicals Corporation of Tarrytown, N.Y. under the trade name IRGACURE® 369; and

COMPOSITION 4 isobornyl acrylate n-hexyl acrylate ethylene glycol diacrylate 2-(4-methyl-benzyl)-2-dimethylamino-1-(4-morpholinophenyl)-1-butanone $R_1R_2$ where 2-(4-methyl-benzyl)-2-dimethylamino-1-(4-morpholinophenyl)-1-butanone is available from Ciba Specialty Chemicals Corporation of Tarrytown, N.Y. under the trade name IRGACURE® 379.

Figure 7:
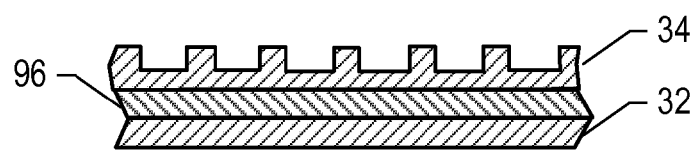
FIG. 7 is a cross-section view showing a primer layer that may be employed in accordance with the present invention.

Referring to FIGS. 2 and 7, it may be desirable to provide substrate 32 with a smooth, if not planar, surface upon which to form imprinting layer 34. To that end, substrate 32 may include a primer layer 96. Primer layer 96 has proved beneficial when surface 36 of substrate 32 appears rough when compared to the features dimensions to be formed in imprinting layer 34. Primer layer 96 may also function, inter alia, to provide a standard interface with imprinting layer 34, thereby reducing the need to customize each process to the imprinting material from which substrate 32 is formed. In addition, primer layer 96 may be formed from an organic imprinting material with the same or different etch characteristics as imprinting layer 34. As a result, primer layer 96 is fabricated in such a manner so as to possess a continuous, smooth, relatively defect-free surface that may exhibit excellent adhesion to imprinting layer 34. An exemplary material to use to form primer layer 96 is available from Brewer Science, Inc. of Rolla Mo. under the trade name DUV30J-6. The primer layer 96 is typically provided with a thickness to facilitate providing the desired surface profile and without being opaque to optical sensing equipment employed to detect patterns, such as alignment marks, on substrate 32 surface.

Figure 8:
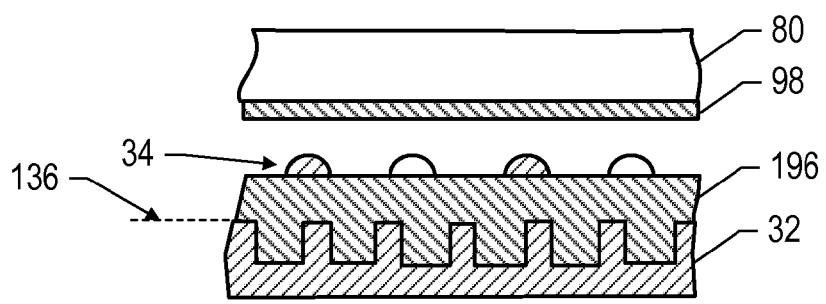
FIG. 8 is a cross-section view showing a release layer applied to a planarization mold.

Referring to FIGS. 7 and 8, it has been found beneficial to deposit a primer layer 196 when an imprinting layer 34 is present upon a surface 136 of substrate 32 that has been previously patterned. To that end, primer layer 196, as with primer layer 96, may be deposited employing any known deposition method, including droplet dispense techniques, spin-on techniques and the like. Furthermore, to enhance the smoothness of the surface of either of primer layer 96 and 196, it may be desired to contact the same with a planarization mold 80 having a substantially smooth, if not planar, contact surface.

To reduce the probability that solidified primer layers 96 and 196 adhere to planarization mold 80, the same may be treated with a low surface energy coating 98. Low surface energy coating 98 may be applied using any known process. For example, processing techniques may include chemical vapor deposition method, physical vapor deposition, atomic layer deposition or various other techniques, brazing and the like. In a similar fashion a low surface energy coating (not shown) may be applied to mold 26, shown in FIG. 2.

In addition to the aforementioned surfactants and low surface energy coatings, fluorinated additives may be employed to improve release properties of the imprinting material. Fluorinated additives, like surfactants, have a surface energy associated therewith that is lower than a surface energy of the imprinting material. An exemplary process by which to employ the aforementioned fluorinated additive is discussed by Bender et al. in MULTIPLE IMPRINTING IN UV-BASED NANOIMPRINT LITHOGRAPHY:RELATED MATERIAL ISSUES, Microelectronic Engineering pp. 61-62 (2002). The low surface energy of the additive provides the desired release properties to reduce adherence of crosslinked and polymerized imprinting material molds 26 and 80.

The embodiments of the present invention described above are exemplary. Many changes and modifications may be made to the disclosure recited above, while remaining within the scope of the invention. For example, the ratio of the components of each of the aforementioned COMPOSITIONs may be varied. The scope of the invention should, therefore, not be limited by the above description, but instead should be determined with reference to the appended claims along with their full scope of equivalents.

What is claimed:

1. An imprint lithography mold assembly, comprising:
   (a) a mold having a surface;
   (b) a substrate having a surface; and
   (c) a polymerizable composition disposed between the surface of the mold and the surface of the substrate, wherein at least a portion of the polymerizable composition is in contact with an oxygen-containing atmosphere between the surface of the mold and the surface of the substrate, and
   wherein the polymerizable composition comprises:
      (i) a plurality of molecules;
      (ii) a photoinitiator; and
      (iii) an oxygen scavenger,
         wherein the photoinitiator is operable to react with oxygen in the oxygen-containing atmosphere during polymerization of the polymerizable compound to form photoinitiator-peroxide radicals,
         wherein the oxygen scavenger is operable to react with the photoinitiator-peroxide radicals formed during polymerization of the polymerizable composition to form an oxygen scavenger radical, and
         wherein the oxygen scavenger radical is operable to facilitate further polymerization and to reduce the formation of photoinitiator-peroxide radicals by reacting with oxygen in the oxygen-containing atmosphere to form additional oxygen scavenger radicals.

2. The imprint lithography mold assembly of claim 1, wherein the oxygen scavenger is selected from a group consisting of 2-methyl-1[4-(methylthio)phenyl]-2-morpholino-propan-1-one-, N-methyldiethanolamine, 2-benzyl-2-dimethylamino-1-(4-morpholinophenyl) -1-butanone, and 2-(4-methyl-benzyl)-2-dimethylamino-1-(4-morpholinophenyl)-1-butanone.

3. The imprint lithography mold assembly of claim 1, wherein the plurality of molecules includes isobornyl acrylate, n-hexyl acrylate, and ethylene glycol diacrylate.

4. The imprint lithography mold assembly of claim 1, wherein the polymerizable composition further comprises a surfactant.

5. The imprint lithography mold assembly of claim 4, wherein the surfactant comprises $R_1R_2$, wherein $R_1$=F$(CF_2CF_2)_y$, with y being in a range of 1 to 7, inclusive, and $R_2$=$CF_2CF_2O(CF_2CF_2O)_xH$, with X in a range of 0 to 15, inclusive.

6. The imprint lithography mold assembly of claim 4, wherein the plurality of molecules includes isobornyl acrylate, n-hexyl acrylate, and ethylene glycol diacrylate.

7. The imprint lithography mold assembly of claim 1, wherein the photoinitiator comprises 2-hydroxy-2-methyl-1-phenyl-propan-1-one.

8. The imprint lithography mold assembly of claim 1, wherein the photoinitiator comprises an amine group.

9. The imprint lithography mold assembly of claim 8, wherein the amine group is photo-active.

10. An imprint lithography mold system, comprising:
    (a) a mold having a surface;
    (b) a substrate having a surface; and
    (c) a polymerizable composition disposed between the surface of the mold and the surface of the substrate, wherein at least a portion of the polymerizable composition is in contact with an oxygen-containing atmosphere between the surface of the mold and the surface of the substrate, and wherein the polymerizable composition comprises:
       (i) a plurality of molecules;
       (ii) a photoinitiator including 2-hydroxy-2-methyl-1-phenyl-propan-1-one; and
       (iii) an oxygen scavenger, wherein the photoinitiator is operable to react with oxygen in the oxygen-containing atmosphere during polymerization of the polymerizable compound to form photoinitiator-peroxide radicals,
       wherein the oxygen scavenger is operable to react with the photoinitiator-peroxide radicals formed during polymerization of the polymerizable composition to form an oxygen scavenger radical, and
       wherein the oxygen scavenger radical is operable to facilitate further polymerization and to reduce the formation of photoinitiator-peroxide radicals by reacting with oxygen in the oxygen-containing atmosphere to form additional oxygen scavenger radicals.

11. The imprint lithography mold assembly of claim 10, wherein the oxygen scavenger is selected from a group consisting of 2-methyl-1[4-(methylthio)phenyl]-2-morpholino-propan-1-one, N-methyldiethanolamine, 2-benzyl-2-dimethylamino-1-(4-morpholinophenyl)-1-butanone, and 2-(4-methyl-benzyl)-2-dimethylamino-1-(4-morpholinophenyl)-1-butanone.

12. The imprint lithography mold assembly of claim 10, wherein the plurality of molecules includes isobornyl acrylate, n-hexyl acrylate, and ethylene glycol diacrylate.

13. The imprint lithography mold assembly of claim 10, wherein the polymerizable composition further comprises a surfactant.

14. The imprint lithography mold assembly of claim 13, wherein the surfactant comprises $R_1R_2$, wherein $R_1$=F$(CF_2CF_2)_y$, with y being in a range of 1 to 7, inclusive, and $R_2$=$CF_2CF_2O(CF_2CF_2O)_xH$, with X in a range of 0 to 15, inclusive.

15. The imprint lithography mold assembly of claim 10, wherein the photoinitiator further includes an amine.

16. The imprint lithography mold assembly of claim 15, wherein the amine is photo-active.

17. An imprint lithography mold system, comprising:
    (a) a mold having a surface;
    (b) a substrate having a surface; and
    (c) a polymerizable composition disposed between the surface of the mold and the surface of the substrate, wherein at least a portion of the polymerizable composition is in contact with an oxygen-containing atmosphere between the surface of the mold and the surface of the substrate, and wherein the polymerizable composition comprises:
       (i) a plurality of molecules;
       (ii) a photoinitiator including an amine group;
       (iii) a surfactant; and
       (iv) an oxygen scavenger,
          wherein the photoinitiator is operable to react with oxygen in the oxygen-containing atmosphere during polymerization of the polymerizable compound to form photoinitiator-peroxide radicals,
          wherein the oxygen scavenger is operable to react with the photoinitiator-peroxide radicals formed during polymerization of the polymerizable composition to form an oxygen scavenger radical, and
          wherein the oxygen scavenger radical is operable to facilitate further polymerization and to reduce the formation of photoinitiator-peroxide radicals by reacting with oxygen in the oxygen-containing atmosphere to form additional oxygen scavenger radicals.

18. The imprint lithography mold assembly of claim 17, wherein the oxygen scavenger is selected from a group consisting of 2-methyl-1-[4-(methylthio)phenyl]-2-morpholino-propan-1-one, N-methyldiethanolamine, 2-benzyl-2-dimethylamino-1(4-morpholinophenyl)-1-butanone, and 2-(4-methyl-benzyl)-2-dimethylamino-1(4-morpholinophenyl)-1-butanone.

19. The imprint lithography mold assembly of claim 17, wherein the plurality of molecules includes isobornyl acrylate, n-hexyl acrylate, and ethylene glycol diacrylate.

20. The imprint lithography mold assembly of claim 17, wherein the surfactant comprises $R_1R_2$, wherein $R_1$=F$(CF_2CF_2)_y$, with y being in a range of 1 to 7, inclusive, and $R_2$=$CF_2CF_2O(CF_2CF_2O)_xH$, with X in a range of 0 to 15, inclusive.

* * * * *